(12) United States Patent
Jones et al.

(10) Patent No.: US 11,445,954 B2
(45) Date of Patent: Sep. 20, 2022

(54) VENOUS ACCESS DEVICE

(71) Applicant: SITE SAVER, INC., Fayetteville, AR (US)

(72) Inventors: Spencer A. Jones, Fayetteville, AR (US); David R. DePoyster, North Little Rock, AR (US); David L. Nichols, Brownsboro, TX (US); Christopher M. Richardson, Athens, TX (US); Kelli L. Shada, Athens, TX (US)

(73) Assignee: Site Saver, Inc., Fayetteville, AR (US)

( * ) Notice: Subject to any disclaimer, the term of this patent is extended or adjusted under 35 U.S.C. 154(b) by 222 days.

(21) Appl. No.: 14/790,386

(22) Filed: Jul. 2, 2015

(65) Prior Publication Data

US 2016/0000363 A1 Jan. 7, 2016

Related U.S. Application Data

(60) Provisional application No. 62/019,968, filed on Jul. 2, 2014.

(51) Int. Cl.
*A61B 5/153* (2006.01)
*A61B 5/145* (2006.01)
(Continued)

(52) U.S. Cl.
CPC .......... *A61B 5/153* (2013.01); *A61B 5/14532* (2013.01); *A61B 5/15003* (2013.01);
(Continued)

(58) Field of Classification Search
CPC .. A61M 25/0014; A61M 25/0026–003; A61M 25/0097; A61M 2025/0031–0035;
(Continued)

(56) References Cited

U.S. PATENT DOCUMENTS 3,670,729 A * 6/1972 Bennett ............. A61M 25/0606
604/164.01
4,037,599 A 7/1977 Raulerson
(Continued)

FOREIGN PATENT DOCUMENTS

EP 0 107 810 5/1984
WO 1999/07301 2/1999
(Continued)

OTHER PUBLICATIONS

World Health Organization, "WHO guidelines on drawing blood: best practices in phlebotomy", 2010.
(Continued)

*Primary Examiner* — Theodore J Stigell
*Assistant Examiner* — Rachel T. Smith
(74) *Attorney, Agent, or Firm* — Evan Law Group LLC

(57) ABSTRACT

A venous access device includes a hub and a bifurcated cannula. The hub includes a bifurcated connecting arm, a blood sampling arm connected to the bifurcated connecting arm, a fluid transfer arm connected to the bifurcated connecting arm, a blood sampling channel and a fluid transfer channel. The blood sampling channel passes through the blood sampling arm and the bifurcated connecting arm. The fluid transfer channel passes through the fluid transfer arm and the bifurcated connecting arm. The bifurcated cannula is coupled to the bifurcated connecting arm and includes a blood sampling lumen having a blood sampling port, a fluid transfer lumen having a fluid transfer port, and a dividing member separating the blood sampling lumen from the fluid transfer lumen. The blood sampling port is 2 mm to 20 mm proximal from the fluid transfer port. The blood sampling channel is fluidly connected to the blood sampling lumen, and the fluid transfer channel is fluidly connected to the fluid transfer lumen.

19 Claims, 9 Drawing Sheets

(51) Int. Cl.
 A61B 5/15 (2006.01)
 A61B 5/155 (2006.01)
(52) U.S. Cl.
 CPC ........ *A61B 5/155* (2013.01); *A61B 5/150068* (2013.01); *A61B 5/150305* (2013.01); *A61B 5/150389* (2013.01); *A61B 5/150396* (2013.01); *A61B 5/150992* (2013.01)
(58) Field of Classification Search
 CPC .. A61M 2025/0037–004; A61M 39/10; A61M 39/105; A61M 5/1582; A61M 2025/0039; A61M 25/0015; A61M 25/007; A61B 5/15003; A61B 5/150389; A61B 5/150992; A61B 5/153; A61B 5/155; A61B 5/150305; A61B 5/150396
 See application file for complete search history.

(56) References Cited

U.S. PATENT DOCUMENTS

| | | | |
|---|---|---|---|
| 4,072,146 A | | 2/1978 | Howes |
| 4,675,004 A * | | 6/1987 | Hadford .............. A61M 5/1582 604/272 |
| 4,776,841 A * | | 10/1988 | Catalano ........... A61M 25/0026 604/43 |
| 5,135,599 A * | | 8/1992 | Martin ............... A61M 25/0009 156/294 |
| 5,480,380 A * | | 1/1996 | Martin ................ A61M 5/1582 604/284 |
| 5,947,953 A * | | 9/1999 | Ash ................... A61M 25/0021 138/115 |
| 6,113,576 A * | | 9/2000 | Dance ................ A61M 25/003 604/164.01 |
| 8,364,231 B2 * | | 1/2013 | Kamath .............. A61B 5/1473 600/347 |
| 9,186,100 B2 | | 11/2015 | Devgon |
| 9,744,344 B1 | | 8/2017 | Devgon |
| 9,750,446 B2 | | 9/2017 | Devgon |
| 10,064,576 B2 | | 9/2018 | Devgon |
| 10,076,272 B2 | | 9/2018 | Devgon et al. |
| 10,300,247 B2 | | 5/2019 | Devgon et al. |
| 2004/0127813 A1 * | | 7/2004 | Schwamm ............. A61B 5/031 600/561 |
| 2004/0167463 A1 | | 8/2004 | Zawacki et al. |
| 2005/0277862 A1 * | | 12/2005 | Anand .................. A61M 1/285 604/4.01 |
| 2006/0004325 A1 * | | 1/2006 | Hamatake ................ A61M 1/16 604/6.01 |
| 2006/0253088 A1 * | | 11/2006 | Chow .................. A61M 25/003 604/284 |
| 2006/0276773 A1 * | | 12/2006 | Wilson .............. A61M 25/0097 604/523 |
| 2007/0078437 A1 * | | 4/2007 | Borden ............. A61M 25/0009 604/523 |
| 2007/0084742 A1 * | | 4/2007 | Miller ................ A61B 17/3472 206/438 |
| 2008/0082136 A1 * | | 4/2008 | Gaudiani ........... A61B 17/3468 607/9 |
| 2012/0197204 A1 * | | 8/2012 | Helm, Jr. .............. A61M 25/02 604/176 |
| 2014/0018772 A1 | | 1/2014 | Ash |
| 2020/0196931 A1 | | 6/2020 | Jones |

FOREIGN PATENT DOCUMENTS

| | | |
|---|---|---|
| WO | 2006/014339 | 2/2006 |
| WO | 2012/075407 | 6/2012 |
| WO | 2016/004307 | 1/2016 |

OTHER PUBLICATIONS

"Peripheral venous catheter", available online at en.wikipedia.org/wiki/Peripheral_venous_catheter, accessed on May 26, 2015.
"Central venous catheter", available online at en.wikipedia.org/wiki/Central_venous_catheter, accessed on May 20, 2015.
"Peripherally inserted central catheter", available online at en.wikipedia.org/wiki/Peripherally_inserted_central_catheter, accessed on May 20, 2015.
"Intravenous therapy", available online at en.wikipedia.org/wiki/Intravenous_therapy, accessed on May 20, 2015.
Moghissi, E.S. et al., "American association of clinical endocrinologists and American Diabetes Association consensus statement on inpatient glycemic control", Endocrine Practice, vol. 15, No. 4, pp. 1-17, (2009).
Adam, K., et al., "Sleep helps healing", British Medical Journal, vol. 289, pp. 1400-1401 (Nov. 24, 1984).
Magaji, V., et al., "Inpatient management of hyperglycemia and diabetes", Clinical Diabetes, vol. 29, No. 1, pp. 3-9, (2011).
Norberg, A., et al., "Contamination rates of blood cultures obtained by dedicated phlebotomy vs intravenous catheter", Journal of the American Medical Association, vol. 289, No. 6, pp. 726-729, (2003).
"Hospital Utilization (in non-Federal short-stay hospitals)", Centers for Disease Control and Prevention, available online at www.cdc.gov/nchs/fastats/hospital.htm, (May 14, 2015).
Shlamovitz, G.Z. et al., "Intravenous Cannulation", available online at emedicine.medscape.com/article/1998177-overview, (May 16, 2015).
"Arrow Twincath® Multiple Lumen Peripheral Catheter Nursing Care Guidelines", Arrow International, available online at www.arrowintl.com/documents/pdf/education/tc-ng0803.pdf, (Jul. 1, 2015).
International Search Report and the Written Opinion dated Oct. 13, 2015 for PCT application No. PCT/US2015/038989.
Behm, S. et al., "Blood draws: A mandate to improve patient experience", Beckers Hospital Review, ASC Communications 2017, 4 pages, found at www.beckershospitalreview.com/quality/blood-draws-a-mandate-to-improve-patient-experience, (2016).
"Save the Vein Campaign", American Nephrology Nurses Association, 3 pages, found at www.annanurse.org/resources/special-projects-and-tools/save-vein-campaign, printed on Jul. 12, 2017.
U.S. Appl. No. 16/805,099, filed Feb. 28, 2020.

* cited by examiner

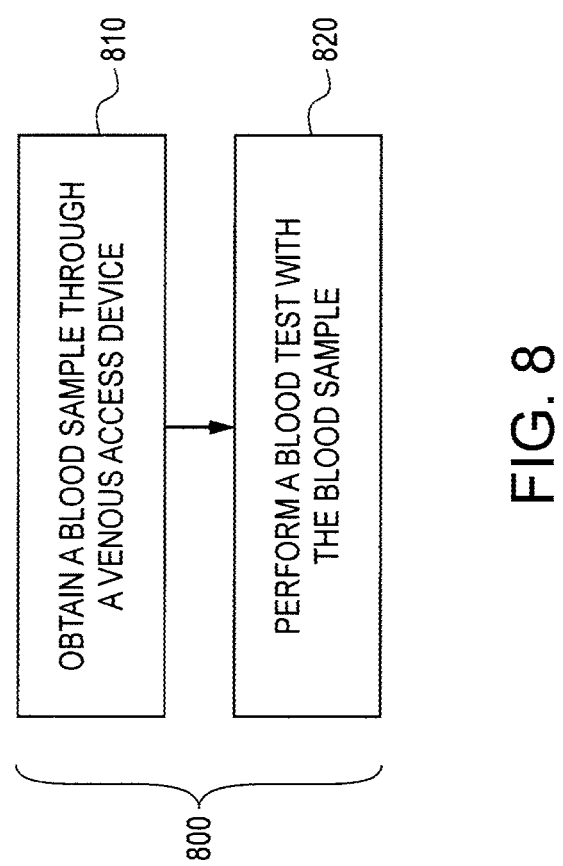

VENOUS ACCESS DEVICE

BACKGROUND

According to the Centers for Disease Control and Prevention (CDC), 35.1 million people are admitted to non-Federal, short-stay hospitals in the United States annually. The vast majority of those patients receive intravenous (IV) therapy to deliver or withdraw fluids such as medications, electrolytes and blood. IV therapy requires the insertion of a venous access device, such as a peripheral venous catheter or a central venous catheter, into a vein. IV therapy is frequently used because it is the fastest way to deliver fluids systemically and because the bioavailability of medicines delivered intravenously is 100%.

A venous access device includes a cannula or catheter inserted through the skin and into a vein. The cannula may be introduced to the vein using a metal trocar or a hypodermic needle to pierce the skin and vein. Once the cannula is advanced to the appropriate location within the vein, the trocar or needle may be removed. The external portion of the cannula may be connected to a syringe or an infusion line, or may be capped or sealed when not in use. A peripheral venous access device is inserted into a peripheral vein, often in the arm or hand, while a central venous access device is placed into a central vein such as the vena cava, internal jugular vein, subclavian vein or femoral vein. Peripheral venous catheters are the most commonly used vascular access devices in medicine.

Some endocrinologists have proposed that all hospitalized patients undergo blood glucose (blood sugar) monitoring since hyperglycemia is often asymptomatic and undiagnosed. Certain hospitalized patients, such as people with diabetes and patients recovering from cardiac surgery, require frequent testing of their blood. The American Association of Clinical Endocrinologists and the American Diabetes Association recommend that hospitalized patients with diabetes have their blood glucose tested every 4 to 6 hours. Furthermore, it is recommended that hospitalized patients receiving intravenous insulin undergo even more frequent blood glucose testing, ranging from every 30 minutes to every 2 hours. A blood sample is typically obtained by a venous blood draw or, for smaller samples such as those used in blood glucose monitoring, a finger prick using a lancet.

Blood sampling has a number of inherent risks. Any skin puncture, whether venous or by finger prick, is painful for a patient. Adverse effects include fainting, loss of consciousness, extravasation, nerve damage, formation of hematomas (bruising) and infiltration (blown vein). Every time that a patient's skin is broken there is a possibility of infection. Blood sampling also carries risks for the medical professional obtaining the sample; handling sharp objects such as hypodermic needles and lancets may result in accidental needle sticks. Medical professionals must be especially careful to avoid needle sticks with used hypodermic needles or lancets to avoid exposure to blood-borne pathogens. Furthermore, the disposable needles and lancets used in blood sampling create a large amount of sharps waste, which must be carefully disposed of. All of these risks are magnified and increased when the frequency of blood sampling is increased.

Frequent blood sampling is expensive due to the large amount of supplies involved. A single hospitalized patient may require 4 to 48 lancets or disposable syringes per day. CDC statistics show that the average hospital stay is 4.8 days, which means that the average diabetic patient will require 20 to 231 lancets while hospitalized. Although blood sampling supplies are inexpensive individually, they represent a considerable expense for hospitals in the aggregate. These costs are ultimately borne by patients and insurers.

A significant problem presented by frequent blood sampling is also the need for overnight sampling. Hospitalized patients that require frequent blood testing must be woken up multiple times throughout the night so that medical professionals may obtain necessary periodic blood samples. These nighttime interruptions can impair a patient's ability to achieve a deep, restorative sleep. Sleep interruption has been shown to slow the healing process and result in longer hospital stays. This is especially problematic for diabetic patients since slower than normal healing is a known complication of diabetes.

One apparent solution to avoid waking a hospitalized patient for multiple venous blood draws or finger pricks is to obtain blood samples from a venous access device that has already been inserted. However, this practice is strongly disfavored. The World Health Organization (WHO) guidelines state that it is acceptable, but not ideal, to draw blood specimens when first inserting a venous access device (WHO Guidelines on Drawing Blood: Best Practices in Phlebotomy, 2010). The WHO guidelines advise against obtaining blood samples from venous access devices that have been used for intravenous therapy because hemolysis, contamination and the presence of intravenous fluid and medication can alter the blood sample results. Blood samples taken from central venous access devices also carry a risk of inaccurate laboratory results and contamination.

SUMMARY

In a first aspect, the invention is a venous access device including a hub and a bifurcated cannula. The hub includes a bifurcated connecting arm, a blood sampling arm connected to the bifurcated connecting arm, a fluid transfer arm connected to the bifurcated connecting arm, a blood sampling channel and a fluid transfer channel. The blood sampling channel passes through the blood sampling arm and the bifurcated connecting arm. The fluid transfer channel passes through the fluid transfer arm and the bifurcated connecting arm. The bifurcated cannula is coupled to the bifurcated connecting arm and includes a blood sampling lumen having a blood sampling port, a fluid transfer lumen having a fluid transfer port, and a dividing member separating the blood sampling lumen from the fluid transfer lumen. The blood sampling port is 2 mm to 20 mm proximal from the fluid transfer port. The blood sampling channel is fluidly connected to the blood sampling lumen, and the fluid transfer channel is fluidly connected to the fluid transfer lumen.

In a second aspect, the invention is a method of performing a blood test, including obtaining a blood sample from a patient through a venous access device, and performing the blood test with the blood sample obtained from the patient through the venous access device.

In a third aspect, the invention is a kit, including a needle and a venous access device. The needle and the venous access device are sterile.

DEFINITIONS

The terms "cannula" and "catheter" are used interchangeably and refer to any tube that is inserted into the body for the purpose of transferring fluids.

The terms "lumen" and "channel" both refer to passages through a structure. Different elements of the venous access device are referred to as lumens or channels for clarity, but both terms have the same meaning.

The term "diabetes" means a metabolic disease characterized by high blood glucose levels (hyperglycemia) over a prolonged period of time. As used herein, "diabetes" includes diabetes mellitus type I, diabetes mellitus type II and gestational diabetes.

The terms "distal" and "proximal" are used to describe a location relative to the hub of the venous access device. For example, the proximal end of the bifurcated cannula is coupled to the hub, and the distal end of the bifurcated cannula is inserted into a patient's vein.

All percentages (%) are weight/weight percentages, unless stated otherwise.

BRIEF DESCRIPTION OF THE DRAWINGS

The invention can be better understood with reference to the following drawings and description.

FIG. 8 illustrates a method of performing a blood test.

The drawings are not to scale. Particularly, the bifurcated cannula appears much larger in the figures than it actually is in the device.

DETAILED DESCRIPTION

There is a need for a blood sampling device that eliminates repeated patient disturbances and painful needle sticks. A venous access device capable of both fluid delivery and blood sampling would significantly reduce many of the adverse issues presented by frequent blood sampling. It would also represent a major cost savings for hospitals. However, a venous blood sampling device must avoid the contamination risks and inaccurate results described in the WHO guidelines.

The present invention is a venous access device that is capable of both transferring fluids and sampling blood intravenously from the same device simultaneously. Applicants have created a venous access device including a bifurcated cannula containing a blood sampling port 2 to 20 millimeters proximal from a fluid transfer port that allows blood samples to be obtained that are not affected by the fluids being transferred. This design eliminates repeated blood draws or finger pricks that have typically been necessary for frequent blood sampling of hospitalized patients. The venous access device reduces patient pain and the potential for adverse effects by decreasing the number of skin punctures. The elimination of sleep interruptions common with traditional overnight blood sampling accelerates patient recovery times. The venous access device significantly reduces costs for hospitals, patients, and insurers by reducing the duration of hospital stays and by minimizing the amount of blood sampling equipment used.

Figure 1:
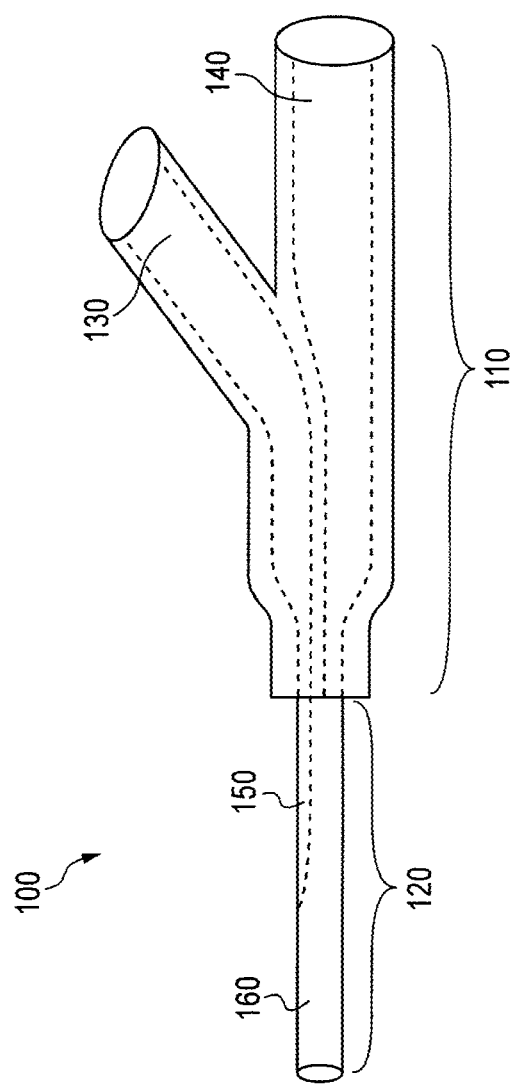
FIG. 1 illustrates a venous access device.

FIG. 1 illustrates a venous access device 100. The venous access device includes a hub 110 and a bifurcated cannula 120. A blood sampling channel 130 and a fluid transfer channel 140 are present in the hub. The bifurcated cannula is coupled to the hub, and includes a blood sampling lumen 150 and a fluid transfer lumen 160. The blood sampling channel and the fluid transfer channel are in fluid connection with the blood sampling lumen and the fluid transfer lumen, respectively. The venous access device may be inserted into a vein in the direction of blood flow in the vein. For example, if the venous access device is inserted into a patient's forearm or hand, the bifurcated cannula will point towards the patient's shoulder and the hub will point towards the patient's fingers. This placement ensures that any fluids being transferred into the vein are carried with the flow of blood towards the heart and that any blood being removed is upstream (farther away from the heart) of the fluid transfer site. Preferably, the venous access device is sterile.

Figure 2:
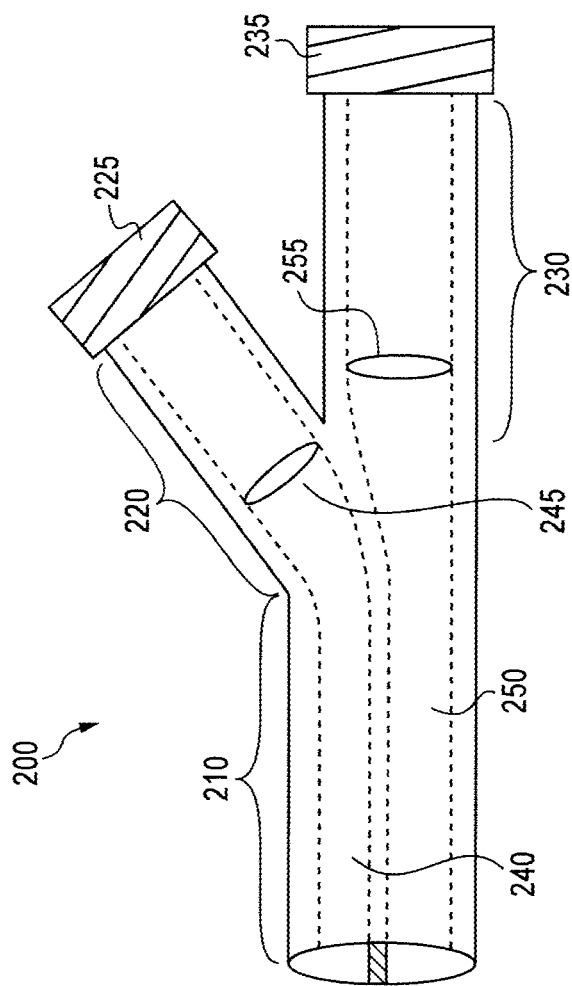
FIG. 2 illustrates a hub.

FIG. 2 illustrates a hub 200. The hub includes a bifurcated connecting arm 210, a blood sampling arm 220 and a fluid transfer arm 230. The blood sampling arm and the fluid transfer arm are both connected to the connecting arm. A blood sampling channel 240 passes through the blood sampling arm and the bifurcated connecting arm. A fluid transfer channel 250 passes through the fluid transfer arm and the bifurcated connecting arm. The hub may be composed of any rigid, durable material. Preferably, the hub is composed of a rigid polymer, but non-rigid polymers or elastomers may also be used. Examples of suitable materials for the hub include polypropylenes, polyethylenes, polycarbonates and polyamides (such as nylon). The hub may be formed by any suitable manufacturing process, such as injection molding or extruding. The bifurcated connecting arm, the blood sampling arm, and the fluid transfer arm may be three discrete parts, or the hub may be a single monolithic component.

The blood sampling arm and the fluid transfer arm may optionally include fittings that allow additional components to connect to the arms. Suitable fittings include Luer fittings, quick connect fittings (also known as quick disconnect couplings), adaptors, plugs, caps, valves and check valves. A preferred fitting is a Luer lock fitting. FIG. 2 shows a first fitting 225 coupled to the blood sampling arm 220, and a second fitting 235 coupled to the fluid transfer arm 230. Alternatively, the fitting may part of the blood sampling arm or the fluid transfer arm, forming a monolithic arm and fitting component.

The blood sampling channel and the fluid transfer channel may optionally include one or more one-way valves to prevent the unintended flow of blood and/or fluids through the channels. The one-way valves are separate from any valves present as fittings attached to the blood sampling arm and/or the fluid transfer arm. FIG. 2 shows a first one-way valve 245 in the blood transfer channel 240, and a second one-way valve 255 in the fluid transfer channel 250.

Figure 3:
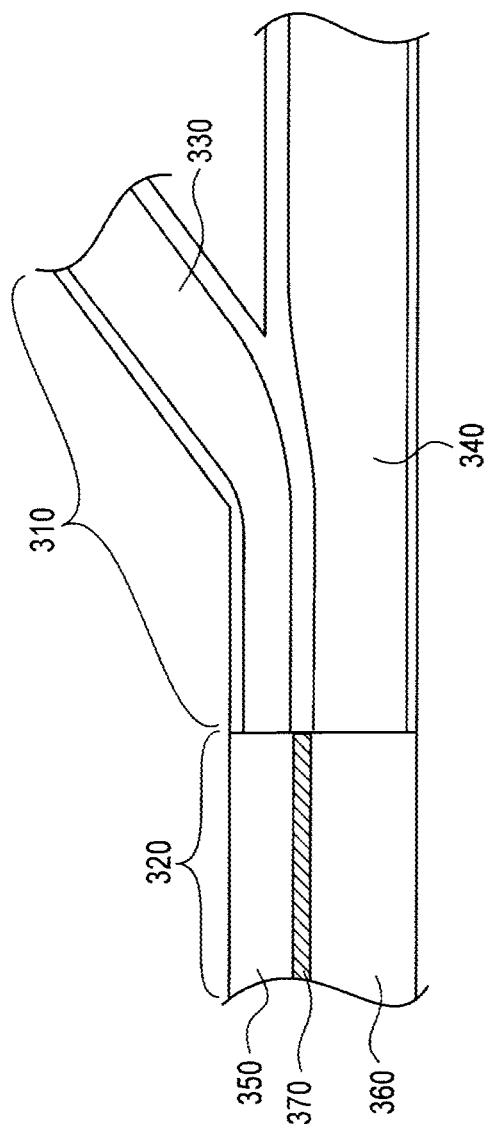
FIG. 3 illustrates a sectioned partial view of a hub coupled to a bifurcated cannula.

FIG. 3 illustrates a sectioned partial view of a hub 310 coupled to a bifurcated cannula 320. The hub may be coupled to the bifurcated cannula using an adhesive or using a coupling member, such as a fitting or an adaptor that connects to both the hub and the bifurcated cannula. A blood sampling channel 330 and a fluid transfer channel 340 are present in the hub. A blood sampling lumen 350 and a fluid transfer lumen 360 are present in the bifurcated cannula and are separated by a dividing member 370. The blood sampling channel is fluidly connected to the blood sampling lumen, and the fluid transfer channel is fluidly connected to the fluid transfer lumen. The separate lumens and channels allow blood to be sampled and fluids to be transferred through the venous access device without mixing, which ensures the blood being sampled is not affected by the fluid being transferred.

Figure 4:
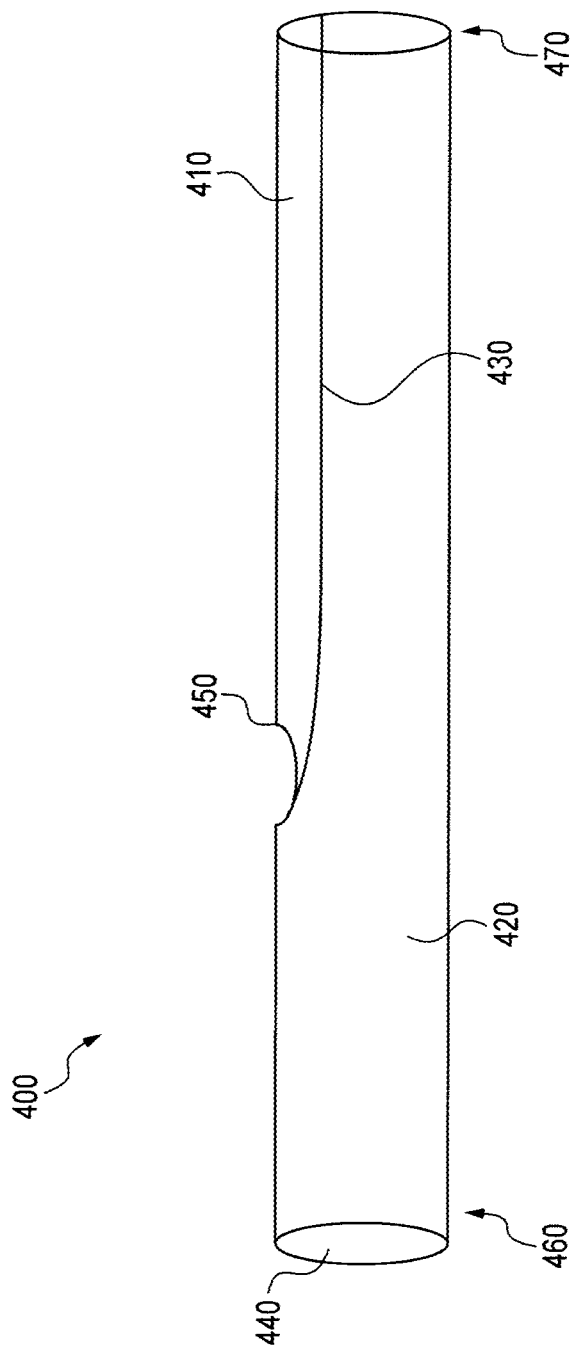
FIG. 4 illustrates a bifurcated cannula.

FIG. 4 illustrates a bifurcated cannula 400. The bifurcated cannula includes a blood sampling lumen 410, a fluid transfer lumen 420 and an internal dividing member 430 separating the blood sampling lumen from the fluid transfer lumen. The fluid transfer lumen has a fluid transfer port 440 and the blood sampling lumen has a blood sampling port 450. The blood sampling port and the fluid transfer port are openings that provide the blood sampling lumen and the fluid transfer lumen, respectively, access to a patient's venous blood. The distal end 460 of the bifurcated cannula is inserted into a patient's vein while the proximal end 470 of the bifurcated cannula remains outside of the patient's vein so that it may be coupled to a hub (not shown).

The blood sampling lumen and the fluid transfer lumen are two distinct spaces within the bifurcated cannula, as illustrated in FIG. 4. The blood sampling lumen may be defined by the dividing member and a portion of the inner surface of the cannula, as shown in FIG. 4. In this configuration, the dividing member tapers from the distal end of the cannula to form the blood sampling lumen within the cannula. The dividing member ensures that the blood sampling lumen is separated from the fluid transfer lumen and that blood and fluids are not mixed within the cannula. Alternatively, the blood sampling lumen may be concentric with the fluid transfer lumen.

The blood sampling port is located 2 to 20 mm proximal from the fluid transfer port, preferably 5 to 16 mm proximal from the fluid transfer port, more preferably 8 to 12 mm proximal from the fluid transfer port. Suitable distances between the blood sampling port and the fluid transfer port include 2, 3, 4, 5, 6, 7, 8, 9, 10, 11, 12, 13, 14, 15, 16, 17, 18, 19 and 20 mm. Greater distances are also possible. The blood sampling port should be located sufficiently apart from the fluid transfer port to obtain a blood sample that does not contain any fluid entering the patient through the fluid transfer lumen. When the bifurcated cannula is inserted into a vein, the blood sampling port will be upstream (farther away from the heart) of the fluid transfer port in relation to the flow of blood through the vein.

The bifurcated cannula may be rigid or flexible. The bifurcated cannula should have some flexibility but must be sufficiently rigid for insertion into a vein. The bifurcated cannula may be composed of any suitable material that is capable of blood and fluid transport and can withstand the venous pressure encountered in healthy patients and those with vascular disease or poor vascular health, typically 5 to 22 mm Hg. Suitable materials for the bifurcated cannula include polyurethanes, polyamides (such as nylon), polyether block amides (PEBA, such as PEBAX®), polytetrafluoroethylenes (PTFE) and BD VIALON® biomaterial (Becton, Dickinson and Company). The bifurcated cannula may be formed by extruding or injection molding. The bifurcated cannula may be provided in a variety of gauge sizes to accommodate adult and pediatric patients. For example, a normal adult patient may receive a 17, 18 or 19 gauge cannula, while a pediatric patient may receive a 20, 21, 22, 23 or 24 gauge cannula. The cannula may be 5 to 100 mm long, preferably 10 to 75 mm long, more preferably 20 to 50 mm long.

Figure 5A:
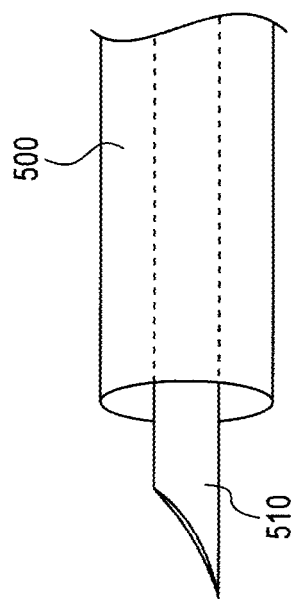
FIG. 5A illustrates a partial view of a bifurcated cannula and a needle in an over-the-needle configuration.
Figure 5B:
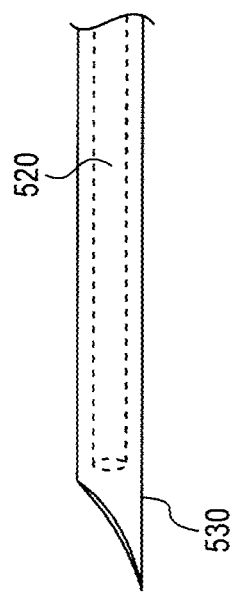
FIG. 5B illustrates a partial view of a bifurcated cannula and a needle in a through-the-needle configuration.

The venous access device may optionally include a needle for penetrating the skin and the vein to insert the cannula. FIG. 5A illustrates a partial view of a bifurcated cannula 500 and a needle 510 in an over-the-needle configuration. FIG. 5B illustrates a partial view of a bifurcated cannula 520 and a needle 530 in a through-the-needle configuration. The needle is composed of metal, preferably stainless steel. The needle may optionally include a cap. The needle may be retractable or non-retractable. Preferably, the needle is sterile.

In an alternative configuration, the hub and the bifurcated cannula may be a monolithic component. A monolithic hub-cannula may be formed by injection molding, extruding or additive manufacturing (3-D printing). The same material may be used for the hub and the bifurcated cannula if it has suitable physical properties for each component. For example, nylon may be an appropriate material for use in producing a monolithic hub-cannula by additive manufacturing. The monolithic hub-cannula may include a retractable needle that retracts into the hub after the cannula has been inserted into a vein.

Figure 6:
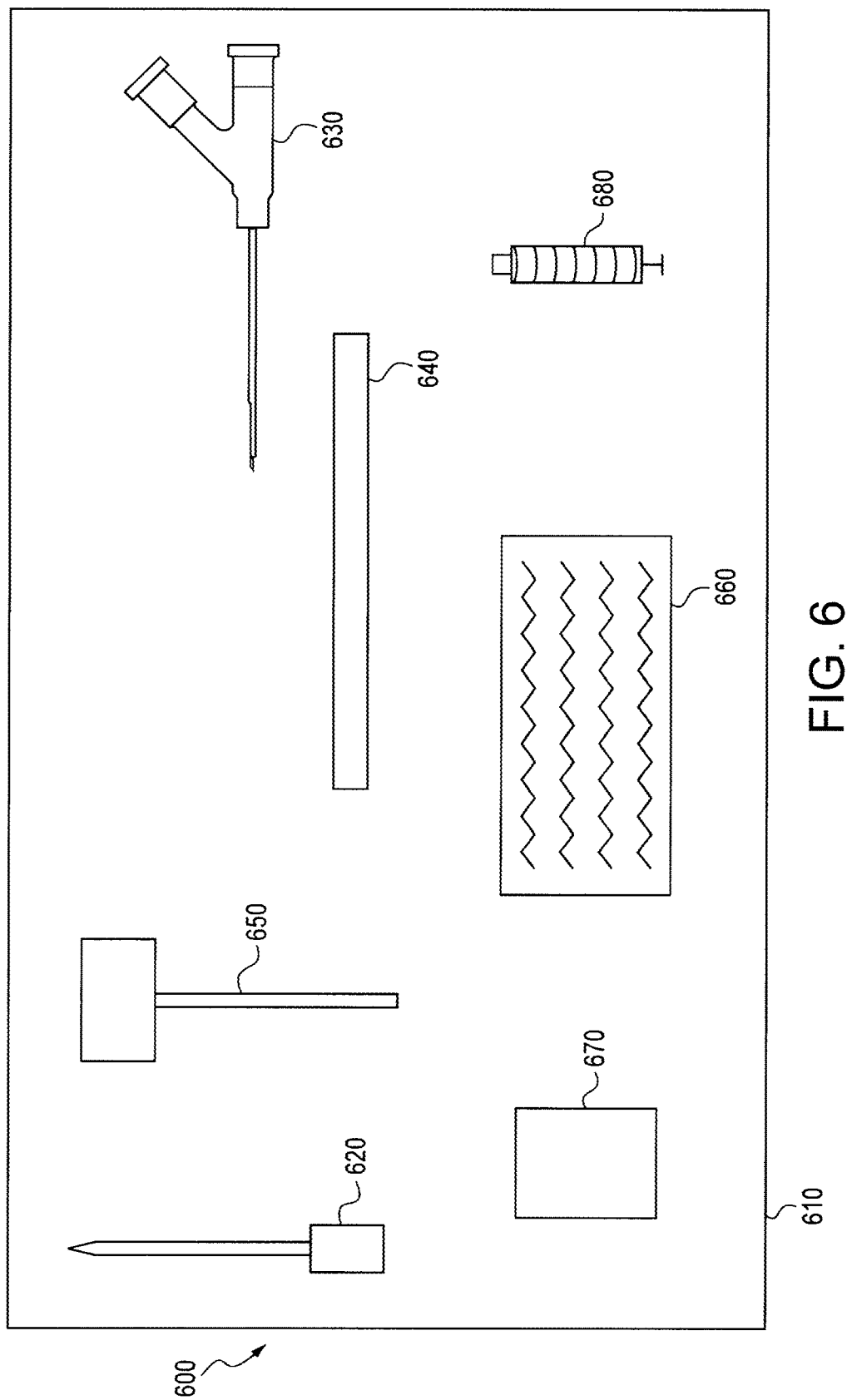
FIG. 6 illustrates a kit for cannulating a patient.

FIG. 6 illustrates a kit 600 for cannulating a patient. The kit is housed in a container 610. The kit contains a needle 620 and a venous access device 630. The kit optionally includes a tourniquet 640 in the form of an elastic strip. An optional antiseptic swab 650 may also be included in the kit. Optional printed instructions 660 describe how to insert and use the venous access device. An optional dressing 670 may be included in the kit. The kit optionally includes flushing materials 680 in the form of a pre-filled syringe. The needle may optionally be a retractable needle. Preferably, the needle, the venous access device and any additional kit components are sterile.

The kit may optionally include a topical antiseptic. For example, the antiseptic may be delivered in a swab, wipe, gel, ointment or spray. The antiseptic may be used to clean the venous access site prior to inserting the needle and cannula. Preferred topical antiseptics include chlorhexidine and alcohol.

The kit may optionally include a tourniquet. The tourniquet may be used to temporarily restrict blood flow near the venous access site and make the vein easier to locate. The tourniquet may be, for example, an elastic strip, an elastic tube, a cloth or a bandage.

The kit may optionally include items for covering the venous access site after the cannula has been inserted into a vein. For example, the kit may contain a transparent dressing, tape or an adhesive bandage.

The kit may optionally include materials for flushing the venous access device after insertion. The kit may include a pre-filled syringe containing a flushing solution, or an empty syringe and a vial or ampoule of flushing solution. A preferred flushing solution is saline. A saline flush may be performed using 5 mL of saline.

The kit may optionally include instructions for use. The instructions may be provided as printed instructions or in electronic format, such as on a universal serial bus (USB) drive, on a secure digital (SD) card, or hosted over the internet and accessible through a quick response (QR) code.

The kit may optionally include a container for housing the kit ingredients. The container protects the needle, venous access device and any other components from damage. The container may be formed of a rigid, durable material such as plastic.

Kits may be provided that contain different sized cannulae for different intended patients. For example, a kit for use in adult patients may contain a 17, 18 or 19 gauge cannula. Similarly, a kit for use in pediatric patients may contain a 20, 21, 22, 23 or 24 gauge cannula.

Figure 7:
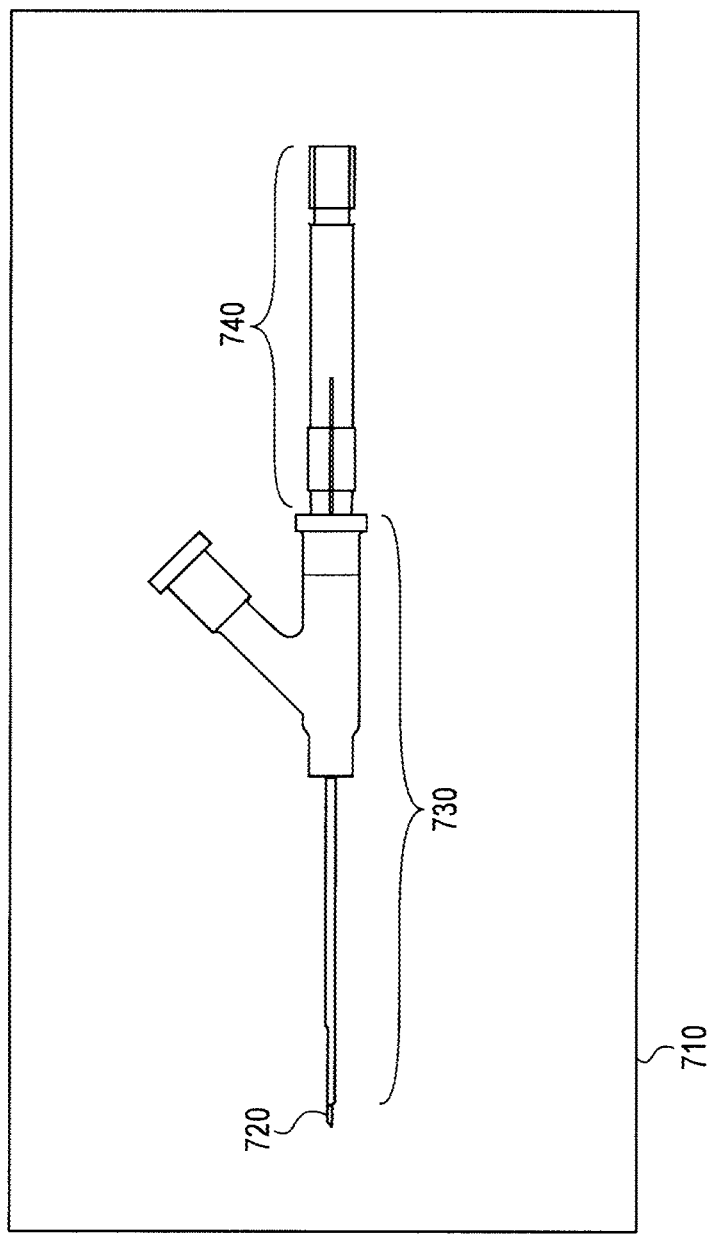
FIG. 7 illustrates an alternative configuration of a kit for cannulating a patient.

FIG. 7 illustrates an alternative configuration of a kit 700 for cannulating a patient. The kit is housed in a container 710. The kit contains a needle 720 that has been pre-threaded through a venous access device 730. The needle includes a cap 740. This configuration is particularly useful when the hub and the bifurcated cannula are a single monolithic component.

Blood samples obtained by the venous access device may be used to perform a number of blood tests. For example, blood samples may be used in a blood glucose test, an amylase test, an antinuclear antibody (ANA) test, a partial thromboplastin time (PTT) test, an international normalized ration (INR) test, a prothrombin time (PT) test, a hemoglobin A1C test, a basic metabolite panel (BMP), a complete blood count (CBC) test, a comprehensive metabolic panel (CMP), an electrolyte test, an erythrocyte sedimentation rate (ESR) test, a flu test, a human chorionic gondadotropin (hCG) test, an HIV antibody test, a lipid profile, a liver panel, a microalbumin test, a prostate-specific antigen (PSA) test or a thyroid-stimulating hormone (TSH) test.

A blood sample may be obtained by attaching a device to the blood sampling arm and applying a negative pressure to the blood sampling channel to draw blood through the blood sampling channel. For example, a medical professional may manually obtain a blood sample without disturbing the patient by attaching a syringe to the blood sampling arm and withdrawing the plunger of the syringe. Alternatively, blood samples may be obtained automatically using an automated sampling device. Such a device may include, for example, a blood testing instrument containing a pump in fluid connection with the blood testing channel. The blood testing instrument may be programmable and capable of obtaining blood samples according to a regular schedule. The venous access device is capable of simultaneous fluid delivery and blood sampling.

FIG. 8 illustrates a method of performing a blood test at 800. First, a blood sample is obtained from a patient through a venous access device at 810. Next, a blood test is performed with the blood sample obtained from the patient through the venous access device 820.

In addition to use in humans, the venous access device may also be used in animals. An appropriately-sized venous access device may be used for fluid transport and blood sampling in an animal in need of intravenous therapy and blood monitoring. The venous access device may be used in the treatment of companion animals, such as dogs and cats, or livestock, such as horses.

EXAMPLES

Example 1—Bench Test in Artificial Hand

An artificial hand including a central tube was chosen to simulate a human hand and the cephalic vein. The central tube was connected to a pump and contained a clear liquid. The pump circulated the clear liquid to simulate blood flow through the cephalic vein. A venous access device including a hub and a bifurcated cannula was inserted into the central tube. The hub included a blood sampling channel and a fluid transfer channel. The bifurcated cannula included a blood sampling lumen having a blood sampling port, a fluid transfer lumen having a fluid transfer port, and a dividing member separating the blood sampling lumen from the fluid transfer lumen. The blood sampling port was 10 mm proximal from the fluid transfer port. A blue dye was introduced to the fluid transfer channel, traveled through the fluid transfer lumen and entered the central tube through the fluid transfer port. The circulating liquid exiting the hand was turned blue by the blue dye. A sample of the circulating liquid was drawn through the blood sampling port and into the blood sampling channel with a syringe. The sampled circulating liquid was clear with no trace of blue dye. The simulation confirmed that the blood sampling port was spaced sufficiently apart from the fluid transfer port to obtain a sample of circulating liquid that was unaffected by the fluid being transferred.

Example 2—Use in Hospitalized Diabetic Patient (Prophetic)

A fifty-year-old male with type II diabetes goes to a hospital emergency room due to chest pains. Once the patient has been admitted, a doctor prescribes intravenous saline and requests that the patient's blood glucose be tested every 2 hours. A nurse prepares the patient for insertion of a venous access device having a hub and a bifurcated cannula. The venous access device will be inserted into the cephalic vein of the patient's left hand. The nurse locates the cephalic vein, applies a tourniquet to the patient's forearm, and swabs the intended venous access site with 2% chlorhexidine. A needle is inserted into the patient's cephalic vein. The bifurcated cannula is advanced over the needle and into the cephalic vein. The needle is removed and the bifurcated cannula is flushed with 5 mL saline. The hub is attached to the bifurcated cannula and the tourniquet is removed. An intravenous saline line is connected to a fluid transfer arm of the venous access device hub and saline is delivered to the patient's cephalic vein. The nurse attaches a syringe to a blood sampling arm of the venous access device hub and draws a blood sample to test the patient's blood glucose. The nurse returns to obtain additional blood samples every two hours as required by the doctor. The patient is able to sleep through the night since the nurse is able to obtain blood samples via the venous access device without waking the patient or pricking his finger while he simultaneously receives intravenous saline.

REFERENCES

1. World Health Organization, "WHO guidelines on drawing blood: best practices in phlebotomy", 2010.
2. "Peripheral venous catheter", available online at en.wikipedia.org/wiki/Peripheral_venous_catheter, accessed on May 26, 2015.
3. "Central venous catheter", available online at en.wikipedia.org/wiki/Central_venous_catheter, accessed on May 20, 2015.
4. "Peripherally inserted central catheter", available online at en.wikipedia.org/wiki/Peripherally_inserted_central_catheter, accessed on May 20, 2015.
5. "Intravenous therapy", available online at en.wikipedia.org/wiki/Intravenous_therapy, accessed on May 20, 2015.
6. Moghissi, E. S. et al., "American Association of Clinical Endocrinologists and American Diabetes Association consensus statement on inpatient glycemic control", Endocrine Practice, Vol. 15, No. 4, pp. 1-17 (May/June 2009).
7. Adam, K., et al., "Sleep helps healing", British Medical Journal, Vol. 289, pp. 1400-1401 (November 24, 2984).
8. Magaji, V., et al., "Inpatient management of hyperglycemia and diabetes", Clinical Diabetes, Vol. 29, No. 1, pp. 3-9 (2011).
9. Norberg, A., et al., "Contamination rates of blood cultures obtained by dedicated phlebotomy vs intravenous catheter", Journal of the American Medical Association, Vol. 289, No. 6, pp. 726-729 (Feb. 12, 2003).

10. "Hospital Utilization (in non-Federal short-stay hospitals)", Centers for Disease Control and Prevention, available online at www.cdc.gov/nchs/fastats/hospital.htm (May 14, 2015).

11. Shlamovitz, G. Z. et al., "Intravenous Cannulation", available online at emedicine.medscape.com/article/1998177-overview (May 16, 2015).

12. "Arrow Twincath® Multiple Lumen Peripheral Catheter Nursing Care Guidelines", Arrow International, available online at www.arrowintl.com/documents/pdf/education/tc-ng0803.pdf (downloaded Jul. 1, 2015).

What is claimed is:

1. A venous access device kit, comprising:
   (a) a hub, comprising,
      (i) a bifurcated connecting arm,
      (ii) a blood sampling arm, connected to the bifurcated connecting arm,
      (iii) a fluid transfer arm, connected to the bifurcated connecting arm,
      (iv) a blood sampling channel, passing through the blood sampling arm and the bifurcated connecting arm, and
      (v) a fluid transfer channel, passing through the fluid transfer arm and the bifurcated connecting arm,
   (b) a bifurcated cannula having an internal dividing member separating a blood sampling lumen from a fluid transfer lumen, coupled to the bifurcated connecting arm, comprising,
      (i) the blood sampling lumen, having a blood sampling port, and
      (ii) the fluid transfer lumen, having a fluid transfer port, and
   (c) a needle, positioned in the fluid transfer lumen,
   wherein the blood sampling port is 15 mm to 20 mm proximal from the fluid transfer port,
   the bifurcated cannula has a length of 20 to 75 millimeters,
   the bifurcated cannula is a 17 to 24 gauge cannula,
   the blood sampling channel is fluidly connected to the blood sampling lumen,
   the fluid transfer channel is fluidly connected to the fluid transfer lumen,
   the bifurcated cannula is flexible,
   the bifurcated cannula has a distal end and the distal end is blunt, and
   the bifurcated cannula and the hub are a monolithic component.

2. The venous access device kit of claim 1, further comprising a fitting coupled to the blood sampling arm.

3. The venous access device kit of claim 1, further comprising a fitting coupled to the fluid transfer arm.

4. The venous access device kit of claim 1, wherein the bifurcated cannula is a 17, 18 or 19 gauge cannula.

5. The venous access device kit of claim 1, wherein the bifurcated cannula is a 20, 21, 22, 23 or 24 gauge cannula.

6. The venous access device kit of claim 1, wherein the hub comprises a material selected from the group consisting of polypropylenes, polyethylenes, polycarbonates and polyamides.

7. The venous access device kit of claim 1, wherein the bifurcated cannula comprises a material selected from the group consisting of polyurethanes, polyamides, polyether block amides (PEBA) and, polytetrafluoroethylenes (PTFE).

8. The venous access device kit of claim 1, wherein the blood sampling port is 18 mm to 20 mm proximal from the fluid transfer port.

9. The venous access device kit of claim 8, wherein the bifurcated cannula has a length of 50 to 75 mm.

10. The venous access device kit of claim 1, wherein the bifurcated cannula includes only the blood sampling lumen and the fluid transfer lumen.

11. A venous access device, comprising:
    (a) a hub, comprising,
       (i) a bifurcated connecting arm,
       (ii) a blood sampling arm, connected to the bifurcated connecting arm,
       (iii) a fluid transfer arm, connected to the bifurcated connecting arm,
       (iv) a blood sampling channel, passing through the blood sampling arm and the bifurcated connecting arm, and
       (v) a fluid transfer channel, passing through the fluid transfer arm and the bifurcated connecting arm, and
    (b) a bifurcated cannula having an internal dividing member separating a blood sampling lumen from a fluid transfer lumen, coupled to the bifurcated connecting arm, comprising,
       (i) the blood sampling lumen, having a blood sampling port, and
       (ii) the fluid transfer lumen, having a fluid transfer port,
    wherein the blood sampling port is at least 15 mm proximal from the fluid transfer port,
    the bifurcated cannula has a length of 20 to 75 millimeters,
    the bifurcated cannula is a 18 to 24 gauge cannula,
    the blood sampling channel is fluidly connected to the blood sampling lumen, and
    the fluid transfer channel is fluidly connected to the fluid transfer lumen,
    the bifurcated cannula is flexible,
    the bifurcated cannula has a distal end and the distal end is blunt, and
    the bifurcated cannula and the hub are a monolithic component.

12. The venous access device of claim 11, further comprising a fitting coupled to the blood sampling arm.

13. The venous access device of claim 11, further comprising a fitting coupled to the fluid transfer arm.

14. The venous access device of claim 11, wherein the bifurcated cannula is a 20, 21, 22, 23 or 24 gauge cannula.

15. The venous access device of claim 11, wherein the hub comprises a material selected from the group consisting of polypropylenes, polyethylenes, polycarbonates and polyamides.

16. The venous access device of claim 11, wherein the bifurcated cannula comprises a material selected from the group consisting of polyurethanes, polyamides, polyether block amides (PEBA) and, polytetrafluoroethylenes (PTFE).

17. The venous access device of claim 11, wherein the blood sampling port is 18 mm to 20 mm proximal from the fluid transfer port.

18. The venous access device of claim 11, wherein the bifurcated cannula has a length of 50 to 75 mm.

19. The venous access device of claim 11, wherein the bifurcated cannula comprises polyurethane.

* * * * *